(12) United States Patent
Mladenov et al.

(10) Patent No.: US 10,653,461 B2
(45) Date of Patent: May 19, 2020

(54) ROD REDUCER

(71) Applicant: K2M, Inc., Leesburg, VA (US)

(72) Inventors: Kiril Mladenov, Sankt Augustin (DE); Brittany Harwell, Warrenton, VA (US)

(73) Assignee: K2M, Inc., Leesburg, VA (US)

( * ) Notice: Subject to any disclaimer, the term of this patent is extended or adjusted under 35 U.S.C. 154(b) by 94 days.

(21) Appl. No.: 15/949,489

(22) Filed: Apr. 10, 2018

(65) Prior Publication Data
US 2018/0221065 A1    Aug. 9, 2018

Related U.S. Application Data

(63) Continuation of application No. 14/996,368, filed on Jan. 15, 2016, now Pat. No. 9,943,344.

(60) Provisional application No. 62/103,626, filed on Jan. 15, 2015.

(51) Int. Cl.
*A61B 17/70* (2006.01)
(52) U.S. Cl.
CPC ...... *A61B 17/7086* (2013.01); *A61B 17/7002* (2013.01)
(58) Field of Classification Search
CPC ....................................... A61B 17/7083–7086
See application file for complete search history.

(56) References Cited

U.S. PATENT DOCUMENTS

| | | |
|---|---|---|
| 2,248,054 A | 7/1941 | Becker |
| 3,604,487 A | 9/1971 | Gilbert |
| 4,263,899 A | 4/1981 | Burgin |
| 5,020,519 A | 6/1991 | Hayes et al. |
| 5,364,397 A | 11/1994 | Hayes et al. |
| 5,420,751 A | 5/1995 | Burns |
| 5,431,658 A | 7/1995 | Moskovich |
| 5,466,243 A | 11/1995 | Schmieding et al. |
| 5,529,571 A | 6/1996 | Daniel |
| 5,685,826 A | 11/1997 | Bonutti |
| 5,720,751 A | 2/1998 | Jackson |

(Continued)

FOREIGN PATENT DOCUMENTS

FR    2985166 A1    7/2013

OTHER PUBLICATIONS

European Search Report EP16151523 dated Jun. 23, 2016.
International Search Report and Written Opinion from Int'l Appl. No. PCT/US14/59425 dated Jan. 12, 2015.

*Primary Examiner* — Nicholas J Plionis
(74) *Attorney, Agent, or Firm* — Lerner, David, Littenberg, Krumholz & Mentlik, LLP

(57) ABSTRACT

A rod reducer including a housing defining an opening, a body member defining an opening and a slot, a shaft disposed through the opening of the housing and coupled to the opening of the body member, an anvil including a linkage extending therefrom, the linkage coupled to the body member and the anvil, a plurality of arm members, and a biasing element disposed between the body member and the anvil. A pin of the linkage is slidably disposed within the slot, and the biasing element is configured to bias the anvil distally with respect to the body member. Rotation of the shaft translates into linear movement, relative to the housing, of the shaft, the body member, and the anvil. The arm members are coupled to the housing and movable towards a parallel configuration as the anvil is advanced away from the housing to engage a bone screw.

18 Claims, 10 Drawing Sheets

(56) References Cited

U.S. PATENT DOCUMENTS

| | | |
|---|---|---|
| 5,910,141 A | 6/1999 | Morrison et al. |
| 5,944,658 A | 8/1999 | Koros et al. |
| 5,951,564 A | 9/1999 | Schroder et al. |
| 6,123,707 A | 9/2000 | Wagner |
| 6,200,322 B1 | 3/2001 | Branch et al. |
| 6,416,521 B1 | 7/2002 | Waldner et al. |
| 6,440,133 B1 | 8/2002 | Beale et al. |
| 6,488,682 B2 | 12/2002 | Kikuchi et al. |
| 6,616,605 B2 | 9/2003 | Wright et al. |
| 6,648,888 B1 | 11/2003 | Shluzas |
| 6,660,006 B2 | 12/2003 | Markworth et al. |
| 6,743,231 B1 | 6/2004 | Gray |
| 6,746,449 B2 | 6/2004 | Jones et al. |
| 6,790,208 B2 | 9/2004 | Oribe et al. |
| 6,790,209 B2 | 9/2004 | Beale et al. |
| 6,849,064 B2 | 2/2005 | Hamada |
| 6,923,814 B1 | 8/2005 | Hildebrand et al. |
| 6,929,606 B2 | 8/2005 | Ritland |
| 6,932,822 B2 | 8/2005 | Oribe et al. |
| 6,957,758 B2 | 10/2005 | Aranyi |
| 7,008,422 B2 | 3/2006 | Foley et al. |
| 7,011,660 B2 | 3/2006 | Sherman et al. |
| 7,083,621 B2 | 8/2006 | Shaolian et al. |
| 7,156,849 B2 | 1/2007 | Dunbar et al. |
| 7,160,300 B2 | 1/2007 | Jackson |
| 7,179,261 B2 | 2/2007 | Sicvol et al. |
| 7,188,626 B2 | 3/2007 | Foley et al. |
| 7,226,453 B2 | 6/2007 | Chao et al. |
| 7,250,052 B2 | 7/2007 | Landry et al. |
| 7,371,239 B2 | 5/2008 | Dec et al. |
| 7,462,182 B2 | 12/2008 | Lim |
| 7,473,267 B2 | 1/2009 | Nguyen et al. |
| 7,481,813 B1 | 1/2009 | Purcell |
| 7,491,207 B2 | 2/2009 | Keyer et al. |
| 7,491,208 B2 | 2/2009 | Pond, Jr. et al. |
| 7,497,869 B2 | 3/2009 | Justis |
| 7,520,879 B2 | 4/2009 | Justis et al. |
| 7,547,318 B2 | 6/2009 | Birkmeyer et al. |
| 7,563,264 B2 | 7/2009 | Landry et al. |
| 7,572,264 B2 | 8/2009 | Null et al. |
| 7,575,581 B2 | 8/2009 | Lovell |
| 7,588,575 B2 | 9/2009 | Colleran et al. |
| 7,588,588 B2 | 9/2009 | Spitler et al. |
| 7,591,836 B2 | 9/2009 | Dick et al. |
| 7,608,081 B2 | 10/2009 | Abdelgany |
| 7,611,517 B2 | 11/2009 | Lim |
| 7,618,442 B2 | 11/2009 | Spitler et al. |
| 7,621,918 B2 | 11/2009 | Jackson |
| 7,625,379 B2 | 12/2009 | Puno et al. |
| 7,637,914 B2 | 12/2009 | Stern |
| 7,651,502 B2 | 1/2010 | Jackson |
| 7,655,008 B2 | 2/2010 | Lenke et al. |
| 7,666,189 B2 | 2/2010 | Gerber et al. |
| 7,691,132 B2 | 4/2010 | Landry et al. |
| 7,708,763 B2 | 5/2010 | Selover et al. |
| 7,776,040 B2 | 8/2010 | Markworth et al. |
| 7,854,751 B2 | 12/2010 | Sicvol et al. |
| 7,887,541 B2 | 2/2011 | Runco et al. |
| 7,909,835 B2 | 3/2011 | Oribe et al. |
| 7,922,749 B2 | 4/2011 | Dewey |
| 7,927,334 B2 | 4/2011 | Miller et al. |
| 7,946,982 B2 | 5/2011 | Hamada |
| 7,955,355 B2 | 6/2011 | Chin |
| 7,988,694 B2 | 8/2011 | Barrus et al. |
| 8,002,798 B2 | 8/2011 | Chin et al. |
| 8,147,524 B2 | 4/2012 | Piza Vallespir |
| 8,192,438 B2 | 6/2012 | Garamszegi |
| 8,230,863 B2 | 7/2012 | Ravikumar et al. |
| 8,298,138 B2 | 10/2012 | Gorek et al. |
| 8,303,595 B2 | 11/2012 | Jones |
| 8,308,729 B2 | 11/2012 | Nunley et al. |
| 9,198,698 B1 * | 12/2015 | Doose ................. A61B 17/708 |
| 9,468,476 B2 * | 10/2016 | Boachie-Adjei ..... A61B 17/708 |
| 9,943,344 B2 | 4/2018 | Mladenov et al. |
| 2002/0052603 A1 | 5/2002 | Nichols et al. |
| 2003/0225408 A1 | 12/2003 | Nichols et al. |
| 2004/0147937 A1 | 7/2004 | Dunbar et al. |
| 2004/0215190 A1 | 10/2004 | Nguyen et al. |
| 2004/0230191 A1 | 11/2004 | Frey et al. |
| 2004/0267275 A1 | 12/2004 | Cournoyer et al. |
| 2005/0059969 A1 | 3/2005 | McKinley |
| 2005/0143749 A1 | 6/2005 | Zalenski et al. |
| 2005/0149053 A1 | 7/2005 | Varieur et al. |
| 2005/0192587 A1 | 9/2005 | Lim |
| 2005/0192589 A1 | 9/2005 | Raymond et al. |
| 2005/0261702 A1 | 11/2005 | Oribe et al. |
| 2005/0277934 A1 | 12/2005 | Vardiman |
| 2006/0025769 A1 | 2/2006 | Dick et al. |
| 2006/0036254 A1 | 2/2006 | Lim |
| 2006/0036260 A1 | 2/2006 | Runco et al. |
| 2006/0074418 A1 | 4/2006 | Jackson |
| 2006/0089651 A1 | 4/2006 | Trudeau et al. |
| 2006/0200132 A1 | 9/2006 | Chao et al. |
| 2006/0253120 A1 * | 11/2006 | Anderson ............ A61B 17/808 606/86 R |
| 2006/0271050 A1 | 11/2006 | Piza Vallespir |
| 2007/0016193 A1 | 1/2007 | Ritland |
| 2007/0055247 A1 | 3/2007 | Jahng |
| 2007/0093817 A1 | 4/2007 | Barrus et al. |
| 2007/0213716 A1 | 9/2007 | Lenke et al. |
| 2007/0213722 A1 | 9/2007 | Jones et al. |
| 2007/0270811 A1 | 11/2007 | Dewey |
| 2007/0270867 A1 | 11/2007 | Miller et al. |
| 2007/0276379 A1 | 11/2007 | Miller et al. |
| 2007/0282337 A1 | 12/2007 | Garamszegi |
| 2008/0015601 A1 | 1/2008 | Castro et al. |
| 2008/0172062 A1 | 7/2008 | Donahue et al. |
| 2009/0018593 A1 | 1/2009 | Barrus et al. |
| 2009/0143828 A1 | 6/2009 | Stad et al. |
| 2009/0228053 A1 | 9/2009 | Kolb et al. |
| 2011/0054259 A1 | 3/2011 | Gorek et al. |
| 2011/0118791 A1 | 5/2011 | Nunley et al. |
| 2011/0166606 A1 * | 7/2011 | Stihl .................. A61B 17/7086 606/279 |
| 2011/0172714 A1 | 7/2011 | Boachie-Adjei et al. |
| 2012/0083853 A1 | 4/2012 | Boachie-Adjei et al. |
| 2012/0277808 A1 | 11/2012 | May |
| 2013/0041228 A1 | 2/2013 | Gorek et al. |
| 2013/0046344 A1 | 2/2013 | Nunley et al. |
| 2014/0163625 A1 | 6/2014 | Meyer et al. |

* cited by examiner

ROD REDUCER

CROSS-REFERENCE TO RELATED APPLICATIONS

The present application is a continuation of U.S. patent application Ser. No. 14/996,368, filed on Jan. 15, 2016, now U.S. Pat. No. 9,943,344, which claims priority to, and the benefit of, U.S. Provisional Application Ser. No. 62/103,626, filed on Jan. 15, 2015, the entire contents of each of which are incorporated herein by reference.

BACKGROUND

Technical Field

The present disclosure relates to orthopedic surgery apparatus for stabilizing and fixing the bones and joints of the body. Particularly, the present disclosure relates to a manually operated rod reducer for reducing a spinal rod into a bone screw in a controlled and measured manner.

Description of Related Art

The spinal column is a complex system of bones and connective tissues that provide support for the human body and protection for the spinal cord and nerves. The human spine is comprised of thirty-three vertebrae at birth and twenty-four as a mature adult. Between each pair of vertebrae is an intervertebral disc, which maintains the space between adjacent vertebrae and acts as a cushion under compressive, bending and rotational loads and motions.

There are various disorders, diseases, and types of injury that the spinal column may experience in a lifetime. The problems may include, but are not limited to, scoliosis, kyphosis, excessive lordosis, spondylolisthesis, slipped or ruptured disc, degenerative disc disease, vertebral body fracture, and tumors. Persons suffering from any of the above conditions typically experience extreme or debilitating pain and often times diminished nerve function.

One of the more common solutions to any of the above mentioned conditions involves a surgical procedure known as spinal fusion. A spinal fusion procedure involves fusing two or more vertebral bodies in order to stabilize or eliminate motion at the intervertebral disc or joint. To achieve this, natural or artificial bone, along with a spacing device, replaces either part or the entire intervertebral disc to form a rigid column of bone, which is stabilized by mechanical hardware.

The mechanical hardware used to immobilize the spinal column typically involves a series of bone screws or anchors, and metal rods or plates. When the spine surgery is performed posteriorly, it is common practice to place bone screws into the vertebral bodies and then connect a metal rod between adjacent vertebral bodies. When the spine surgery is performed anteriorly, it is common practice to attach a thin metal plate directly to the vertebral bodies and secure it to each vertebral level using one or more bone screws.

The process of properly inserting the spinal rod into the receiving slot of one or more bone screws, followed by securing the connecting rod therein, often requires the clinician to use a number of instruments and expend a great deal of time and effort. The repeated process of inserting and securing the spinal rod into one or more bone screws secured to adjacent vertebrae can be difficult, tiresome, and time consuming. Further, alignment of the spinal rod as it's connected between sequential bone screws may require adjustment, and therefore, it is desirable that an apparatus and method be provided by which the spinal rod can be reduced into the screw housing of each of the sequentially aligned bone screws and, as necessary, provide for adjustment so as to facilitate the process for the clinician with minimal effort and loss of time. Therefore, a need exits for an efficient way to reduce the spinal rod into the screw housing and lock the spinal rod in place.

SUMMARY

The present disclosure is directed to a rod reducer including a housing having an opening, a body member defining an opening, and a shaft disposed through the opening of the housing and coupled to the opening of the body member. The rod reducer further includes an anvil including a linkage extending therefrom, the linkage coupled to the anvil and the body member, where a pin of the linkage is slidably disposed within the slot of the body member. A biasing element configured to bias the anvil distally with respect to the body member is disposed between the body member and the anvil. Additionally, first and second arm members are coupled to the housing and are configured to engage a bone screw. First and second arm members are movable towards a parallel configuration as the anvil is advanced away from the housing. The rod reducer is configured such that rotation of the shaft translates into linear movement of the shaft relative to the housing.

In one embodiment, the biasing element is a compression spring.

In one embodiment, the biasing element applies between 1 pound-force and 30 pounds-force to the anvil.

In a further embodiment, the pin of the linkage is configured to slide between a first end of the slot and a second end of the slot. In yet another embodiment, when the pin is disposed at the first side of the slot the linkage is configured to drive the anvil distally, and when the pin is disposed at the second side of the slot the linkage is configured to drive the anvil proximally. In another embodiment, the anvil and the biasing element are configured to transition the pin of the linkage from the second end of the slot to the first end of the slot upon the anvil subjected to a proximally directed force.

In one embodiment, the linkage is coupled to an aperture of the anvil. In another embodiment, the linkage and the anvil are monolithically formed.

In yet another embodiment, the biasing element is disposed about the linkage.

In one embodiment, the first and second arm members are pivotably coupled to the housing.

In a further embodiment, a receiving saddle is disposed on the anvil, such that the receiving saddle cooperatively engages with a surface of a spinal rod. In another embodiment, the receiving saddle is generally formed into an arch, and is configured to engage with a variety of spinal rod diameters.

In one embodiment, a head at a proximal end of the shaft is configured to cooperatively engage with a drive tool.

In another aspect of the present disclosure, a method for reducing a spinal rod includes, coupling first and second arm members of a first rod reducer to a first bone screw. The method further includes positioning a spinal rod between an anvil of the first rod reducer, the first and second arm members of the first rod reducer, and a screw housing of the first bone screw. The method further includes rotating a shaft of the first rod reducer such that the shaft translates distally with respect to a housing of the first rod reducer and the arm members grasp the housing of the first bone screw. The method also includes rotating the shaft of the first rod reducer such that the anvil of the first rod reducer is brought into contact with an outer surface of the spinal rod. The method further includes biasing the anvil of the first rod reducer distally with respect to the body member of the first rod reducer against the outer surface of the spinal rod via a biasing element of the first rod reducer disposed between the anvil and the body member. The method further includes driving distally, via rotation of the shaft, the body member of the first rod reducer, a linkage of the first rod reducer, and the anvil of the first rod reducer. The body member is coupled to the shaft and the linkage is coupled between the body member and the anvil.

In an embodiment, the method further includes absorbing and dampening a proximally directed force exerted by the spinal rod against the anvil of the first rod reducer. In a further embodiment, absorbing and dampening the proximally directed force further includes sliding a pin of the linkage within a slot of the body member between a first end and a second end of the slot.

In yet another embodiment, the method includes maintaining abutment between the anvil of the first rod reducer and the outer surface of the spinal rod via the distal bias of the biasing element.

In another embodiment, the method further includes coupling first and second arm members of a second rod reducer to a second bone screw. Further, the method includes positioning the spinal rod between an anvil of the second rod reducer, the first and second arm members of the second rod reducer, and a screw housing of the second bone screw. Additionally, the method includes rotating a shaft of the second rod reducer such that the shaft translates distally with respect to a housing of the second rod reducer and the arm members grasp the housing of the second bone screw. The method includes rotating the shaft of the second rod reducer such that the anvil of the second rod reducer is brought into contact with the outer surface of the spinal rod. The method includes biasing the anvil of the second rod reducer distally with respect to a body member of the second rod reducer against the outer surface of the spinal rod via a biasing element of the second rod reducer disposed between the anvil and the body member.

In one embodiment, the method further includes maintaining abutment between the anvil of the second rod reducer and the outer surface of the spinal rod via the distal bias of the biasing element of the second rod reducer during the distal driving of the body member, linkage, and anvil of the first rod reducer.

In yet another embodiment, the method includes rotating the shaft of the first rod reducer such that the shaft translates proximally with respect to the housing of the first rod reducer, and decoupling the arm members of the first rod reducer from the first bone screw.

BRIEF DESCRIPTION OF THE DRAWINGS

The above and other aspects and features of the present disclosure will become more apparent in light of the following detailed description when taken in conjunction with the accompanying drawings in which.

DETAILED DESCRIPTION OF EMBODIMENTS

Figure 3:
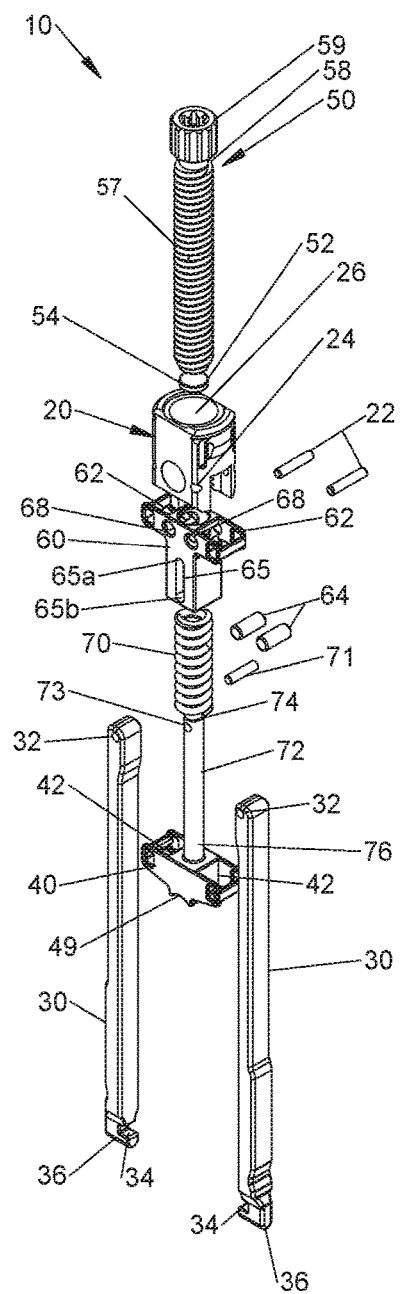
FIG. 3 is a perspective view, with parts separated, of the rod reducer of FIGS. 1 and 2.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" will refer to the portion of the or component thereof that is closer to the clinician and the term "distal" will refer to the portion of the or component thereof that is farther from the clinician. Additionally, in the drawings and in the description that follows, terms such as front, rear, upper, lower, top, bottom, and similar directional terms are used simply for convenience of description and are not intended to limit the disclosure.

Figure 2:
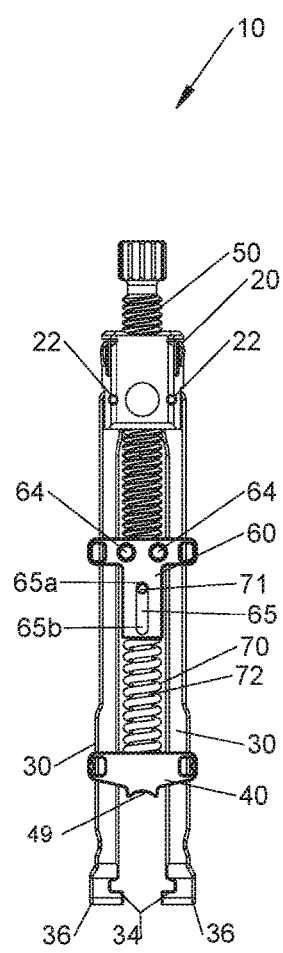
FIG. 2 is a front view of the rod reducer of FIG. 1 in a second orientation with the body, the anvil, and the biasing element in a second configuration.
Figure 1:
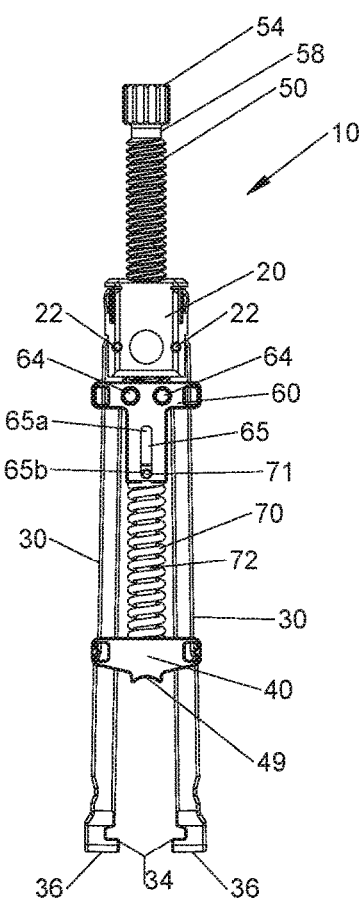
FIG. 1 is a front view of a rod reducer in accordance with the present disclosure with the rod reducer in a first orientation and a body, an anvil, and a biasing element of the rod reducer in a first configuration.

Referring initially to FIGS. 1-3, a rod reducer in accordance with the present disclosure is generally designated as rod reducer 10. Rod reducer 10 includes a housing 20, a plurality of arm members 30, an anvil 40, a shaft 50 coupled to a body member 60, and a biasing element 70 disposed between the anvil 40 and the body member 60. With further reference to FIGS. 4-7, rod reducer 10 may include two arm members 30. Each arm member 30 is insertable through a respective cavity 42 of the anvil 40 and cavity 62 of the body member 60. Arm members 30 are pinned in place relative to housing 20 with pins 22. Alternatively, it is contemplated that arm members 30 may be integrally formed with housing 20 such that, rather than pivoting relative to housing 20, arm members 30 flex relative to housing 20. In such an embodiment, pins 22 may be omitted and arms 30 may be directly attached to housing 20. Pins 22 extend through a respective pin hole 24 of the housing 20 and a respective pin hole 32 of each arm member 30. Pin holes 32 in combination with pins 22 and pin holes 24 define a pivot axis for first and second arm members 30. As seen in FIG. 6, each arm member 30 has a hook portion 34 at its distal end 36 for engaging a screw housing 100 that is disposed at a proximal end of a bone screw BS (as seen in FIGS. 9A-10C). During reduction of a spinal rod 200 into screw housing 100, arm members 30 move from a first orientation being spaced apart with respect to each other (FIG. 1) towards a parallel orientation and ending in a second orientation (FIG. 2), such that hook portion 34 of each respective arm member 30 may engage bone screw BS (as seen in FIGS. 9A-10C). Engagement of hook portion 34 to bone screw BS serves to maintain alignment of rod reducer 10 with respect to the screw housing 100 as spinal rod 200 is reduced therein.

Figure 4:
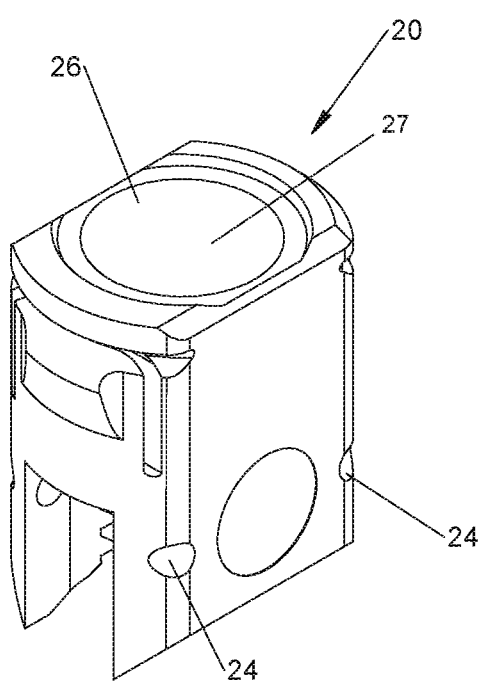
FIG. 4 is a perspective view of a housing of the rod reducer of FIG. 1.
Figure 5:
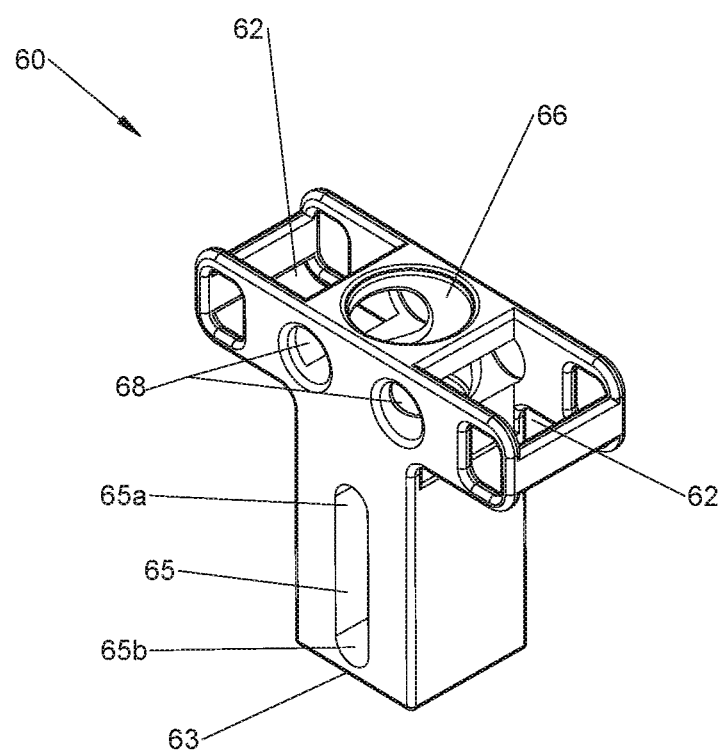
FIG. 5 is a perspective view of a body member of the rod reducer of FIG. 1.
Figure 6:
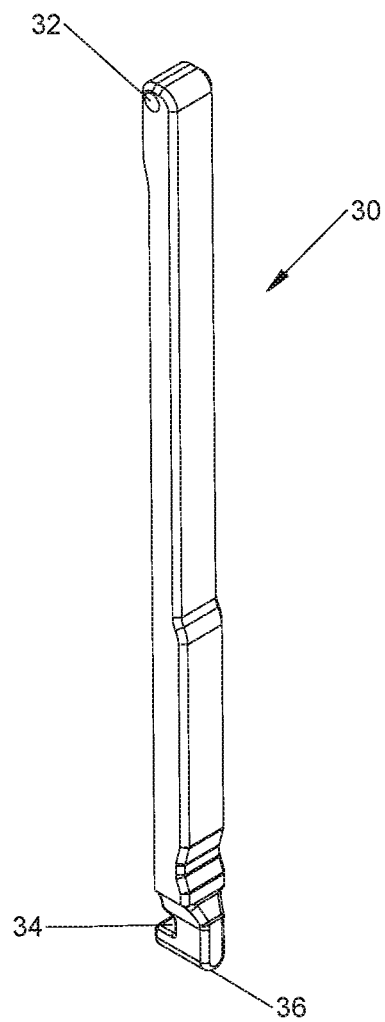
FIG. 6 is a perspective view of an arm member of the rod reducer of FIG. 1.

With reference to FIGS. 3-5, shaft 50, body member 60, and the coupling thereof, will be described. Shaft 50 has threads 57 thereon and includes a distal portion 54 with an annular groove 52 and a proximal portion 58 with a head 59. It is envisioned that head 59 may be configured to cooperatively engage with any number of counterpart drive tools known in the art to effect torque driven rotation. For example, head 59 may be configured to receive a hex head (as shown in FIG. 3) or a Philips or slotted screwdriver. Shaft 50 is insertable through an opening 26 of housing 20 such that the distal portion 54 of shaft 50 is receivable within an aperture 66 of body member 60. Pins 64 are used to maintain the shaft 50 within the aperture 66 of body member 60 by inserting pins 64 through pin holes 68 of body member 60 such that a portion of each pin 64 resides in the annular groove 52 at the distal end 54 of shaft 50.

Figure 7:
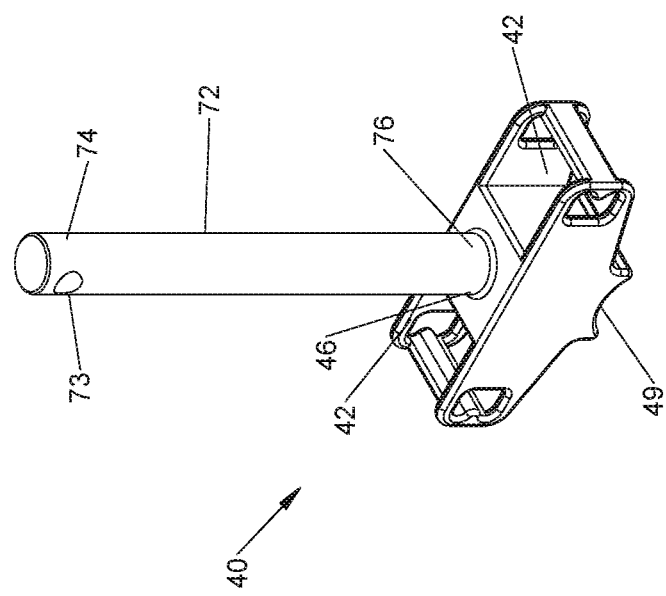
FIG. 7 is a perspective view of an anvil and a linkage of the rod reducer of FIG. 1.
Figure 8:
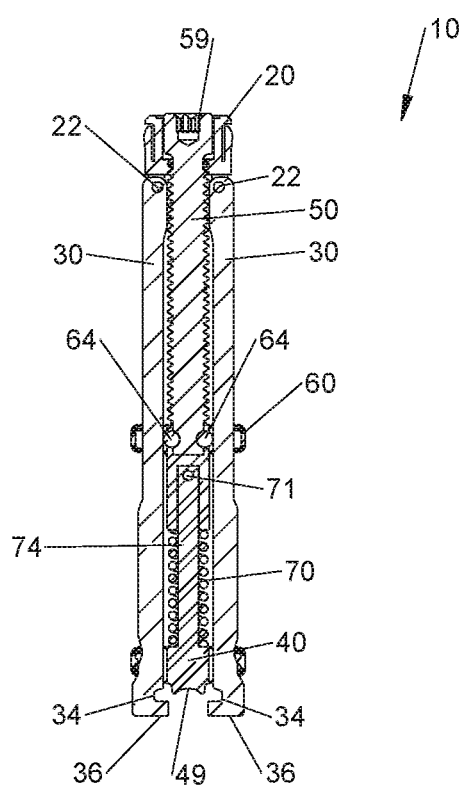
FIG. 8 is a cross-sectional view of the rod reducer of FIG. 1 with the anvil and the body member in a distal most position, and the body, the anvil, and the biasing element in the second configuration.

With reference to FIGS. 3, 5, and 7, the coupling of anvil 40, body member 60, and biasing element 70 will be described. A linkage 72 couples anvil 40 and body member 60, where biasing element 70 is disposed between anvil 40 and body member 60. It is envisioned that biasing element 70 may be disposed about linkage 72, such that linkage 72 provides axial strength thereto when biasing element 70 undergoing compressive stress, as discussed below. A first end 74 of linkage 72 is slidably received with a distal cavity 63 of body member 60. It is envisioned that linkage 72 and anvil 40 may be monolithically formed, such that linkage 72 extends therefrom, or alternatively a second end 76 of linkage 72 may be coupled to an aperture 46 of anvil 40. A pin 71 insertable within a pinhole 73 disposed at the first end 74 of linkage 72 is configured to slide within a slot 65 of body member 60 between a first end 65a (FIG. 2) and a second end 65b (FIG. 1) of slot 65, as will be described further below.

When coupled, shaft 50, body member 60, biasing element 70, linkage 72, and anvil 40 form an associated structure and cooperatively act to reduce spinal rod 200. More particularly, threads 57 of shaft 50 engage corresponding threads 27 (not explicitly shown) of opening 26 of housing 20, such that rotation of shaft 50 with respect to housing 20 results in proximal and distal translation of shaft 50 with respect to housing 20. Threads 57 and 27 of shaft 50 and housing 20, respectively, permit torque driven rotation and proximal and distal translation of the shaft 50 with respect to housing 20. During torque driven rotation of shaft 50, body member 60 may travel towards and away from housing 20 in unison with the proximal and distal translation of shaft 50, where proximal and distal translation of shaft 50 and body member 60 are directly proportional to the threaded configuration of the shaft 50 and the housing 20. During reduction of spinal rod 200 into bone screw BS, threaded rod 50 is manually rotated distally such that body member 60 simultaneously travels distally with respect to housing 20.

Figure 10A:
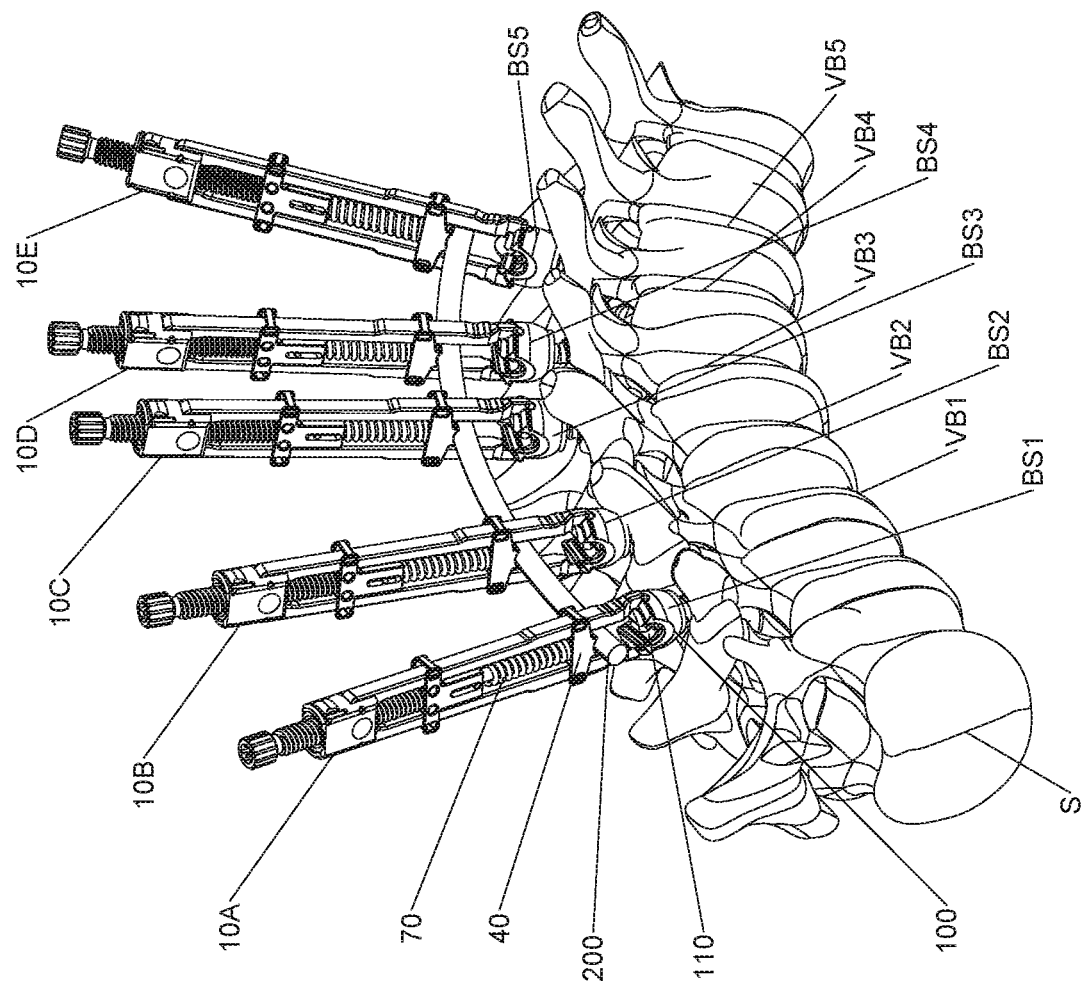
FIG. 10A is a perspective view of a construct including a plurality of rod reducers of FIG. 1 coupled to a plurality of bone screws attached to adjacent vertebrae and a spinal rod.
Figure 10B:
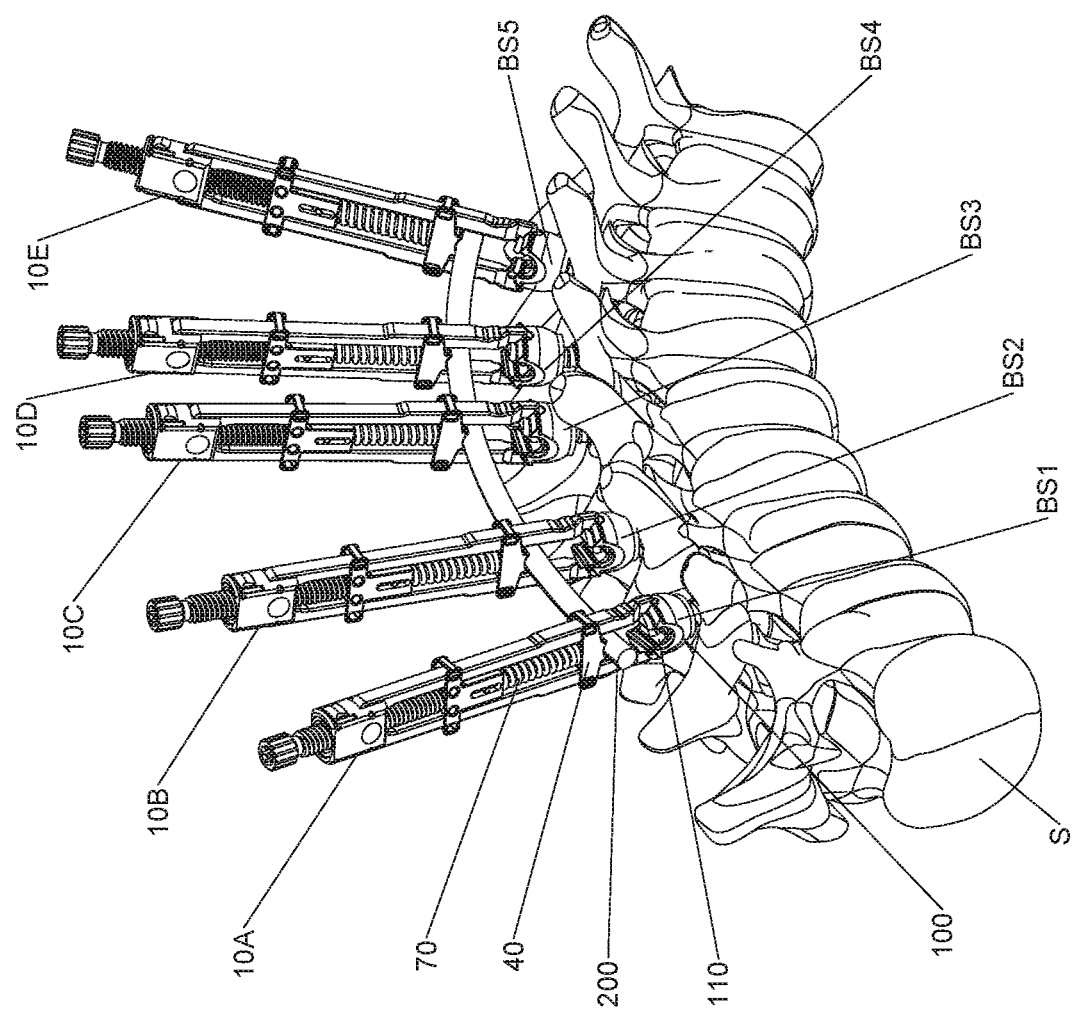
FIG. 10B is a perspective view of the construct of FIG. 10A with the spinal rod partially reduced.
Figure 10C:
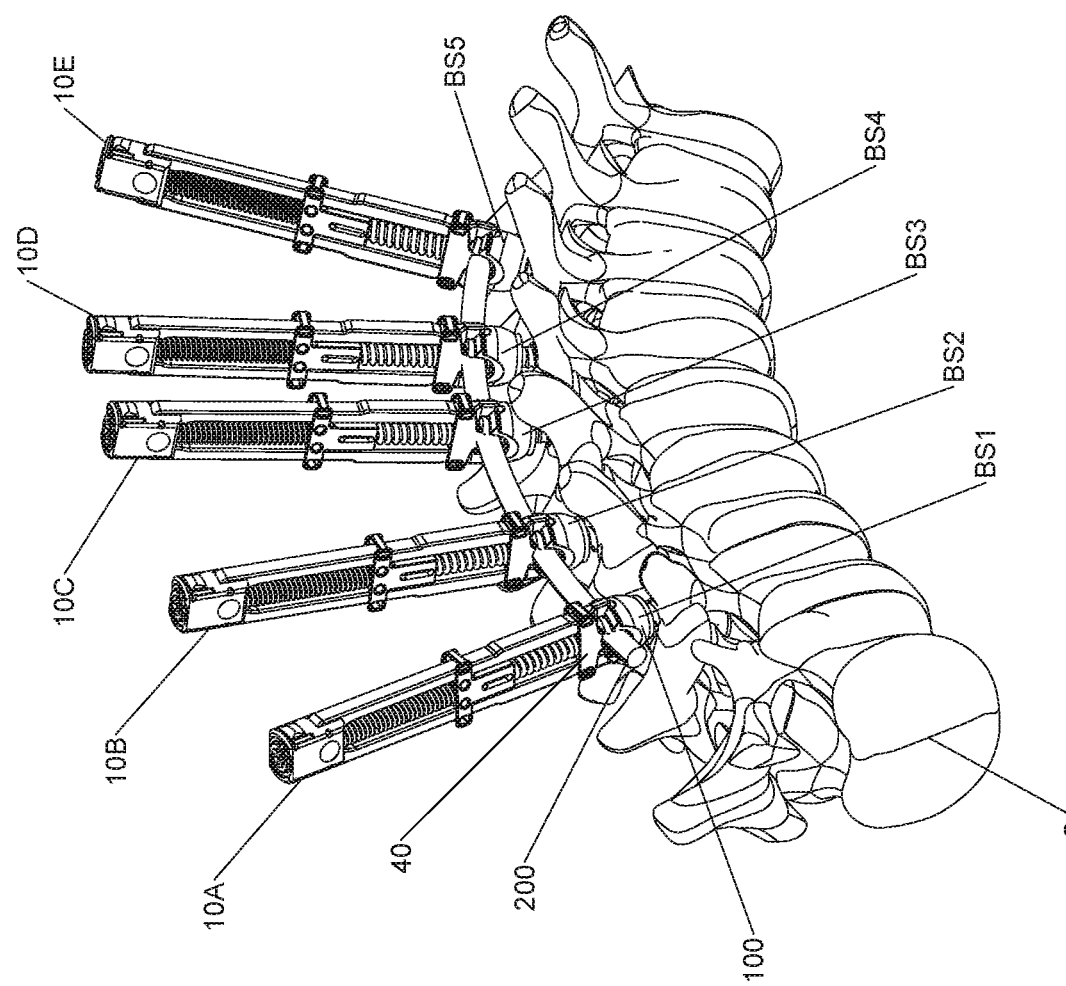
FIG. 10C is a perspective view of the construct of FIG. 10 with the spinal rod completely reduced.

With biasing element 70 disposed between anvil 40 and body member 60, biasing element 70 provides a biasing force therebetween, such that anvil 40 is biased either away from, or towards, body member 60. Biasing element 70 may represent, for example, a compression spring, an extension spring, or any biasing element known in the art. In one embodiment, biasing element 70 imparts or applies a distal biasing force on anvil 40 thereby biasing anvil 40 distally towards bone screw BS. Biasing element 70 may pre-load the anvil 40, thus providing a distally directed force upon the anvil 40 and spinal rod 200 during reduction of spinal rod 200. Biasing element 70 may provide a pre-load force between an approximate range of 1-50 pounds-force (lbf), and more preferably between 1-30 lbf. It is contemplated that the pre-load force may also have values between 1-75 lbf or 1-60 lbf or 1-40 lbf. Biasing element 70 further acts as a dampener during reduction of spinal rod 200, such that a more uniform and constant force is applied thereto via anvil 40 for a smooth reduction. As discussed below, it is envisioned that during an incremental reduction of spinal rod 200 between multiple bone screws BS fixed sequentially to adjacent vertebra, biasing element 70 acts as a dampener to facilitate the reduction of spinal rod 200 therein (FIGS. 10A-10C). More particularly, biasing element 70 serves to distally bias anvil 40 against spinal rod 200, and further, acts to absorb and dampen any resistive forces exerted proximally against anvil 40 by spinal rod 200 during reduction and/or manipulation of spinal rod 200.

Figure 9B:
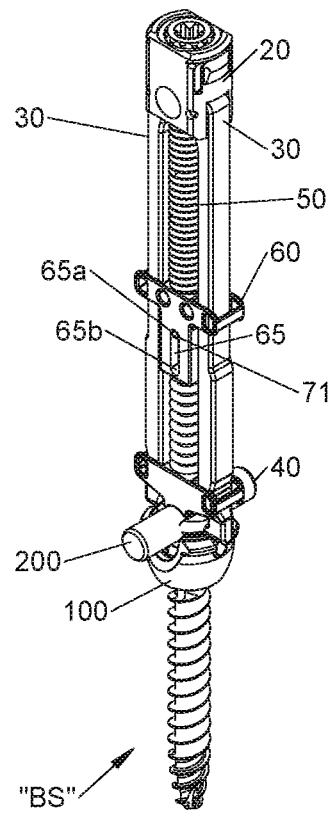
FIG. 9B is a perspective view of the rod reducer of FIG. 9A with the spinal rod completely reduced into the bone screw.
Figure 9A:
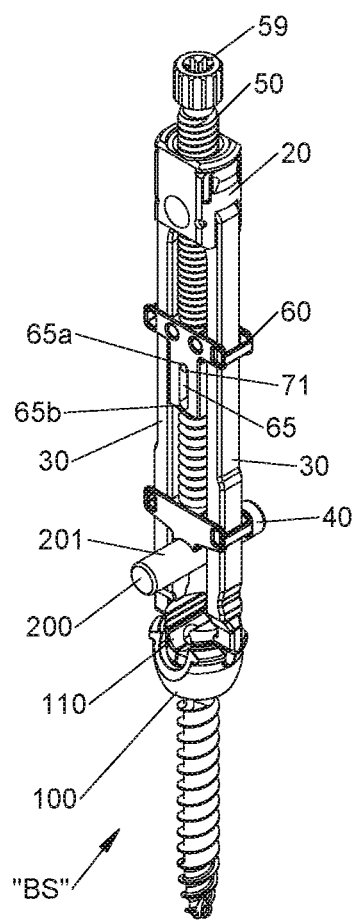
FIG. 9A is a perspective view of the rod reducer of FIG. 1, with the body, the anvil, and the biasing element in the second configuration, and coupled to a bone screw with a spinal rod partially reduced therein.

With reference to FIGS. 7, 9A, and 9B, anvil 40 and spinal rod 200 will be further described. During reduction of spinal rod 200, a receiving saddle 49 of anvil 40 is in abutment with an outer surface 201 of spinal rod 200. It is envisioned that receiving saddle 49 is configured to accommodate a range of spinal rod diameters. For example, receiving saddle 49 may be configured to cooperatively engage with a spinal rod 200 having a variance in diameter of approximate 3 mm to 8 mm, while still achieving the necessary driving force to secure the spinal rod 200 into a bone screw BS. Receiving saddle 49 may be generally arched or convex, but may take the form of any geometric shape adapted to cooperatively engage with and drive a spinal rod during reduction.

During reduction of spinal rod 200, and proximal and distal translation of body member 60, biasing element 70 applies proximal and distal bias to anvil 40, thereby causing anvil 40 to translate proximally and distally (i.e., towards and away from seat or saddle portion 110 of bone screw BS; see FIGS. 9A-10C). As body member 60 translates proximally and distally, biasing element 70 acts to pull anvil 40 proximally and drive anvil 40 distally, respectively. It is further envisioned that anvil 40 may additionally, or alternatively, be pulled proximally and driven distally by linkage 72 as a result of the position of pin 71 within slot 65. With pin 71 in abutment with the first end 65a of slot 65, linkage 72 may supplement the distal driving force of biasing element 70 upon anvil 40. With pin 71 in abutment with the second end 65b of slot 65, linkage 72 may supplement the proximal driving force of biasing element 70 upon anvil 40.

Further, if anvil 40 encounters proximal resistance during a procedure, the proximal resistance applied to anvil 40 causes pin 71 to slide proximally within slot 65 from second end 65b to first end 65a. As body member 60 translates distally bringing anvil 40 into contact with spinal rod 200 such that a distal force is applied thereon, anvil 40 and biasing element 70 may encounter resistance from spinal rod 200. The resulting resistance (i.e., a proximal load against anvil 40) acts to compress biasing element 70, thus driving pin 71 proximally from the second end 65b of slot 65 (a first configuration of pin 71) towards the first end 65a of slot 65 (a second configuration of pin 71).

More particularly, as body member 60 translates distally, biasing element 70 biases, and drives, anvil 40 distally towards spinal rod 200, free of any proximal resistance. With anvil 40 free of any proximal resistance, pin 71 is at, or near, the second end 65b of slot 65 (the first configuration). As anvil 40 is brought into contact with spinal rod 200, anvil 40 encounters proximal resistance. With anvil 40 under a proximal load, pin 71 slides proximally within slot 65 towards, or into abutment with, first end 65a (the second configuration). With pin 71 at the first end 65a, continued distal translation of body member 60 causes linkage 72 to drive anvil 40 distally. Conversely, as body member 60 translates proximally pin 71 slides from the first end 65a towards the second end 65b, and biasing element 70 initially maintains the distal force upon anvil 40. With pin 71 at the second end 65b, continued proximal translation of body member 60 causes biasing element 70 and/or linkage 72 to pull anvil 40 proximally. As should be appreciated, during the reduction of spinal rod 200 into bone screw BS biasing element 70 serves to maintain the distal bias upon anvil 40, such that any proximal resistance encountered by anvil 40 is absorbed and dampened by the distal bias created from biasing element 70. Accordingly, distal translation of shaft 50 results in distal translation of body member 60 and anvil 40 attached thereto, resulting in the reduction of spinal rod 200 into bone screw BS.

With reference to FIGS. 1, 2, 9A, and 9B, the interaction between arm members 30, anvil 40, and body member 60 will be further described. Proximal and distal translation of anvil 40, via proximal and distal translation of body member 60, causes each arm member 30 to pivot with respect to housing 20 about their respective pin holes 32. In an alternate embodiment, each arm member 30 flexes relative to housing 20 as anvil 40 is translated proximally and distally with respect to housing 20. As anvil 40 travels distally from a proximal most position (FIG. 1) to a distal most position (FIG. 9B), with respect to housing 20, arm members 30 move from the first orientation (FIG. 1) towards the parallel orientation and into the second orientation (FIGS. 2 and 9A-10C). Once arm members 30 move towards the parallel orientation, hook portion 34 of each respective arm member 30 acts to engage the screw housing 100 of bone screw BS.

Arm members 30, anvil 40, body member 60 and biasing element 70 will now be described with respect to proximal and distal translation of shaft 50. As noted above, proximal and distal translation of shaft 50 results in proximal and distal translation of body member 60 to effect reduction of spinal rod 200 into screw housing 100 of bone screw BS. As seen in FIG. 1, body member 60 and anvil 40 are in the proximal most position, respectively, and arm members 30 are in the first orientation and may be engaged or unengaged from screw housing 100 of bone screw BS. As seen in FIGS. 2 and 9A-10C, body member 60 and anvil 40 are an intermediate position between their respective proximal most and distal most positions, and arm members 30 are in the second orientation and securely engaged with the screw housing 100 of bone screw BS. As seen in FIG. 9B, body member 60 and anvil 40 are in the distal most position, respectively, arm members 30 are in the second orientation, pin 71 is in the second configuration, and spinal rod 200 is fully reduced within screw housing 100 of bone screw BS.

During reduction of spinal rod 200, biasing element 70 maintains a distal bias upon anvil 40 and thus spinal rod 200, and further dampens any proximally directed forces or resistance encountered by anvil 40. As illustrated in FIGS. 1, 2, and 9A-10C, as body member 60 and anvil 40 translate between their respective proximal and distal most positions, as a result of proximal resistance encountered by anvil 40, pin 71 slides proximally and distally within slot 65 of body member 60 between the first end 65a (i.e., the second configuration) and the second end 65b (i.e., the first configuration). The distal bias provided by biasing element 70 acts to maintain contact between anvil 40 and spinal rod 200, and further ease the reduction of spinal rod 200 within screw housing 100 by better distributing the load applied by anvil 40 against spinal rod 200 and minimize point loading therebetween.

Operating a rod reducer in accordance with the present disclosure will be described with reference to FIGS. 1-10C. A spinal rod and screw construct is assembled in a patient as follows. A clinician implants bone screw BS into a spinal vertebra "VB" with screw housings 100 of the bone screw BS positioned to receive a portion of spinal rod 200 in seat 110 of the screw housing 100. It is envisioned that a clinician may implant multiple bone screw "BS1-n" sequentially into several adjacent spinal vertebra "VB1-n" during a procedure (FIGS. 10A-10C). Once the desired number of bone screws BS have been implanted, the clinician aligns and manipulates the spinal rod 200 such that a portion of the spinal rod 200 is in proximal relation to the screw housing 100 of each respective bone screws BS, such that spinal rod 200 creates an unbroken connection between each bone screw BS.

The clinician next positions rod reducer 10 into proximity with each respective bone screw BS, such that hook portion 34 of arm members 30 of rod reducer 10 is in near abutment to the screw housing 100 of each respective bone screw BS. Next, the clinician causes the hook portion 34 of the arm members 30 to grasp, clip, or otherwise affix to the screw housing 100, such that during reduction of spinal rod 200 attachment of the rod reducer 10 to the bone screw BSn, and alignment of spinal rod 200 to the screw housing 100, is maintained. During reduction, spinal rod 200 is positioned between the screw housing 100, the anvil 40, and the arm members 30, and may be in abutment to the anvil 40 (as seen in FIGS. 9A, 10A, and 10B) or in abutment to the screw housing 100 (as seen in FIG. 9B, 10C).

The clinician next reduces spinal rod 200 into the seat 110 of screw housing 100. Often times there may be 15 mm or more of travel required in order to reduce spinal rod 200 fully within the seat 110 of screw housing 100 such that spinal rod 200 and screw housing 100 can be locked. The clinician is provided a mechanical advantage of torque driven rotation via shaft 50 to facilitate reduction and securement of spinal rod 200 within bone screw BS. However, rotating shaft 50 such a distance can be cumbersome, tedious, and time consuming. The distal bias to anvil 40 provided by biasing element 70 eases the reduction of spinal rod 200. The load or force provided by biasing element 70 upon anvil 40, and thus spinal rod 200, aids to maintain the position of, and connection between, anvil 40 and spinal rod 200. Biasing element 70 further acts to distribute the load caused by anvil 40 upon spinal rod 200, and minimize point loading therebetween.

When utilizing multiple bone screws BS and rod reducers 10, biasing element 70 of each respective rod reducer 10 further serves to dampen any proximally directed forces exerted upon anvil 40 of each respective rod reducer from spinal rod 200. More particularly, with a plurality of rod reducers 10, where each rod reducer 10 is mounted to a different bone screw BS, the clinician is able to gradually or incrementally reduce the spinal rod 200 into each respective bone screws BS by sequentially reducing each rod reducer 10 until all rod reducers 10 have been fully reduced and spinal rod 200 is completely reduced into all of the adjacent bone screws BS. With the rod reducer 10 attached to bone screw BS, it is further envisioned that the clinician may use rod reducer 10 to further assist the alignment of spinal rod 200 between multiple bone screws BS. The clinician is provided a mechanical advantage to further bend or shape spinal rod 200 while spinal rod 200 is securely held by both rod reducer 10 and the screw housing 100 of the bone screw BS. In this configuration, the clinician may make final adjustments to the spinal rod 200 when connecting spinal rod 200 between multiple bone screws BS. After spinal rod 200 is properly aligned, the clinician may further reduce spinal rod 200 to secure the spinal rod 200 into the screw housing 100 of the bone screw BS.

With reference to FIGS. 10A-10C, a screw construct for reducing spinal rod 200 into multiple bone screws BS will be described which includes a plurality of bone screws BS1-BS5 and a plurality of rod reducers 10A-10E. Initially, bone screws BS1-BS5 are implanted sequentially into adjacent vertebrae VB1-VB5. Prior to any correction of spinal rod 200, the surgeon can manipulate and correct the curve of the spinal column S to a large degree. The spinal rod 200 can be pre-bent to the configuration of the normal spinal curve, e.g., the sagittal curve. Once certain the spine S is in the desired anatomical orientation, the surgeon can position the pre-bent spinal rods 200 relative to bone screws BS1-BS5 and rod reducers 10A-10E, and reduce spinal rod 200 into a first point of the spinal column, e.g., VB1, where the construct is to be attached. Rod reducers 10A-10E may be sequentially reduced, alternating from the ends toward the middle, from one end to the other, or any combination thereof depending upon the surgeon's technique to reduce spinal rod 200 into the screw housing 100 of each respective bone screw BS1-BS5. It is noted that rod reducers 10A-10E may also be contemporaneously reduced and need not be reduced sequentially.

It should be appreciated that as one or more rod reducers 10A-10E reduce spinal rod 200, anvil 40 of rod reducers 10 actively reducing spinal rod 200, and additionally anvil 40 of rod reducers 10 simply coupled to bone screws BS, may undergo resistance and/or encounter a proximally directed force from spinal rod 200. Conversely, spinal rod 200 moves distally away from, and out of contact with, anvil 40 as portions of spinal rod 200 are driven into proximity with a respective bone screw BS, such as, for example, during sequential reduction of spinal rod 200. As spinal rod 200 moves out of contact with anvil 40 of a respective rod reducer 10, the attachment between rod reducer 10 and bone screw BS may loosen or become completely decoupled. As should be appreciated, the abutment of anvil 40 against spinal rod 200 provides axial stability between rod reducer 10 and bone screw BS during reduction. As such, the distal bias of anvil 40 caused by biasing element 70 enhances the connection between anvil 40 and spinal rod 200, and thus enhances the coupling of rod reducer 10 and bone screw BS. The distal bias and/or pre-load upon anvil 40 created by biasing element 70 absorbs and dampens any proximal resistance exerted by spinal rod 200 against anvil 40, and further maintains contact between anvil 40 and spinal rod 200 thus increasing axial stability to enhance the attachment between rod reducer 10 and bone screw BS.

As illustrated in FIGS. 10A-C, each rod reducer 10A-10E is coupled to a respective bone screw BS1-BS5, where spinal rod 200 is positioned between anvil 40 of each respective rod reducer 10A-10E and screw housing 100 of each respective bone screw BS1-BS5 (i.e., the arms 30 of each respective rod reducer 10A-10E are in the second orientation). As spinal rod 200 is sequential reduced via distal translation of anvil 40 of one or more rod reducers 10A-10E, portions of spinal rod 200 not being actively reduced may exert a force proximally, or alternatively, may move distally towards bone screws BS. As a result, anvil 40 may encounter a proximally directed force from spinal rod 200, or conversely, may be caused to lose contact with spinal rod 200, thus weakening the connection between rod reducer 10 and bone screw BS.

For example, and as illustrated in FIG. 10A, spinal rod 200 may be sequentially reduced into five bone screws BS1-BS5 utilizing five rod reducers 10A-10E. Initially, anvil 40 of each of rod reducers 10A-10E may be brought into contact with spinal rod 200. As rod reducer 10A begins to incrementally reduce spinal rod 200, biasing element 70 serves to distribute the load and minimize point loading caused by the driving of anvil 40 distal against spinal rod 200. Further, as anvil 40 of rod reducer 10A drives spinal rod 200 distally, spinal rod 200 may be caused to move proximally against, or conversely move distally away from and out of contact with, the anvil 40 of rod reducers 10B-10E. In such a situation, biasing element 70 is configured to absorb and dampen any proximally directed forces exerted upon anvil 40 of rod reducers 10B-10E, and further, distally bias anvil 40 to maintain contact between anvil 40 and spinal rod 200. Thus, biasing element 70 not only facilitates the reduction of rod reducer 10A which is actively reducing spinal rod 200, but further serves to stabilize rod reducers 10B-E of the screw construct which are not actively being used to reduce spinal rod 200. It should be appreciated that any of rod reducers 10A-10E may be used to actively reduce spinal rod 200, where the biasing element 70 of the remaining rod reducers 10A-10E serves to maintain the stability of the screw construct. Additionally, this maintains engagement between the rod reducers 10A-10E and their respective bone screws BS1-BS5.

As illustrated in FIG. 10B, all of rod reducers 10A-10E are in a state of incremental reduction of spinal rod 200, where spinal rod 200 is partially reduced. As illustrated in FIG. 10C, spinal rod 200 is fully reduced and anvil 40 of each rod reducer 10A-10E is in the distal most position.

Upon final alignment of spinal rod 200 between one or more bone screws BS, and/or securement of spinal rod 200 into screw housing 100 thereof, the clinician sequentially or contemporaneously rotates shaft 50 of one or more reducers 10 such that the respective shaft 50, body member 60, and anvil 40 attached thereto translate proximally. As the clinician translates body member 60 and anvil 40 towards the proximal most position (FIG. 1), arm members 30 of the respective rod reducer 10 may be decoupled from the screw housing 100, permitting the clinician to detach rod reducer 10 from the respective bone screw BS.

It is envisioned that the clinician may be provided with multiple spinal rods 200. The clinician may perform the method described above to facilitate the reduction of multiple spinal rods 200 into multiple screw housings 100 to a number of vertebrae in sequence. It is further envisioned that the clinician may be provided with multiple bone screws and spinal rods of varying sizes.

In accordance with the present disclosure, a kit will be described with reference to FIGS. 1-10C. The kit includes rod reducer 10 in a package (not shown). The kit may further include bone screw BS, spinal rod 200, an orthopedic tool or device (not shown), and instructions for use. Examples of the orthopedic tool or device may be a tightening or loosening tool, an alignment tube, or a locking device. It is further envisioned, that the kit may include multiple rod reducers 10, multiple bone screws BS, and multiple spinal rods 200. Further, the kit may include a variety of sizes of bone screws BS and spinal rods 200. The package may include a thermoformed plastic tray and/or other packaging materials within the view of those skilled in the art.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of presently disclosed embodiments. Thus, the scope of the embodiments should be determined by the claims of the present application and their legal equivalents, rather than by the examples given.

What is claimed is:

1. A rod reducer comprising:
   a housing defining an opening;
   a body member defining a slot and cavities;
   a shaft received through the opening of the housing and rotatably coupled with the body member;
   first and second arm members coupled to the housing, the first and second arm members extending through the respective cavities of the body member, the first and second arm members transitionable between an approximated position and a spaced apart position;
   a biasing member slidably coupled with the body member; and
   an anvil coupled with the biasing member such that the anvil is biased distally, wherein rotation of the shaft causes axial displacement of the anvil, the axial displacement of the anvil directly transitioning the first and second arm members between the approximated and spaced apart positions.

2. The rod reducer according to claim 1, wherein the biasing member is disposed between the anvil and the body member.

3. The rod reducer according to claim 1, wherein the first and second arm members are movable relative to the housing about respective axes.

4. The rod reducer according to claim 1, wherein the anvil defines cavities dimensioned to receive respective first and second arm members therethrough.

5. The rod reducer according to claim 1, wherein the shaft includes an annular groove, and the body member includes pins dimensioned to be diametrically received in the annular groove of the shaft to rotatably couple the shaft with the body member.

6. The rod reducer according to claim 1, wherein the anvil includes a linkage configured to receive the biasing member thereabout.

7. The rod reducer according to claim 6, wherein the linkage and the anvil are monolithically formed.

8. The rod reducer according to claim 6, wherein the linkage includes a pin protruding from a proximal portion of the linkage, the pin is dimensioned to be slidably received in the slot of the body member extending along a longitudinal axis defined by the shaft.

9. A rod reducer comprising:
   a housing defining an opening;
   a body member defining an opening and a slot, the body member movable relative to the housing;
   a shaft disposed through the opening of the housing and coupled to the opening of the body member;
   an anvil including a linkage extending therefrom, the linkage movably coupled to the body member, a pin of the linkage slidably disposed within the slot of the body member;
   a biasing element disposed between the body member and the anvil, the biasing element configured to engage the anvil to bias the anvil distally; and
   first and second arm members coupled to the housing, the first and second arm members configured to engage a bone screw, the first and second arm members movable towards a parallel configuration directly from advancement of the anvil away from the housing,
   wherein rotation of the shaft translates the shaft relative to the housing.

10. The rod reducer according to claim 9, wherein the biasing element is a compression spring.

11. The rod reducer according to claim 9, wherein the biasing element applies between about 1 pound-force and about 30 pounds-force to the anvil.

12. The rod reducer according to claim 9, wherein the pin of the linkage is configured to slide between a first end of the slot and a second end of the slot of the body member.

13. The rod reducer according to claim 12, wherein the anvil and the biasing element are configured to transition the pin of the linkage from the second end of the slot to the first end of the slot upon proximal resistance exerted upon the anvil.

14. The rod reducer according to claim 9, wherein the linkage is coupled to an aperture of the anvil.

15. The rod reducer according to claim 9, wherein the biasing element is disposed about the linkage.

16. The rod reducer according to claim 9, wherein the first and second arm members are pivotably coupled to the housing.

17. The rod reducer according to claim 9, further comprising a receiving saddle disposed on the anvil, the receiving saddle configured to cooperatively engage a spinal rod.

18. The rod reducer according to claim 17, wherein the receiving saddle includes an arch configured to engage with the spinal rod.

* * * * *